(12) United States Patent
Inaba et al.

(10) Patent No.: US 8,536,364 B2
(45) Date of Patent: Sep. 17, 2013

(54) METHOD FOR PRODUCING SULFUR-CONTAINING CARBOXYLIC ACID ESTERS

(75) Inventors: Teruhiko Inaba, Kanagawa (JP); Kazuma Hojo, Kanagawa (JP); Kenya Ishida, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 228 days.

(21) Appl. No.: 13/093,133

(22) Filed: Apr. 25, 2011

(65) Prior Publication Data

US 2011/0282089 A1    Nov. 17, 2011

(30) Foreign Application Priority Data

May 13, 2010    (JP) ................. 2010-111483

(51) Int. Cl.
*C07C 327/32* (2006.01)
*C07C 319/02* (2006.01)

(52) U.S. Cl.
USPC .......................... 558/255; 560/147

(58) Field of Classification Search
USPC .......................... 558/255; 560/147
See application file for complete search history.

(56) References Cited

U.S. PATENT DOCUMENTS 5,565,473 A * 10/1996 Belley et al. ............... 514/313
7,105,194 B2    9/2006 Gassenmeier et al.

OTHER PUBLICATIONS

Dia et al. "Flavouring and odorant thiols from renewable natural resources by InIII-catalysed hydrothioacetylation and lipase-catalysed solvolysis" Tetrahedron Letters, 2010, vol. 51, pp. 2164-2167.*

European Search Report issued Apr. 16, 2012 in Application No. 11162998.6.

K. R. Hebditch et al., "Synthesis of Isotopically Labelled Thiol Volatiles and Cysteine Conjugates for Quantification of Sauvignon Blanc Wine", Journal of Labelled Compounds and Radiopharmaceuticals, vol. 50, No. 4, pp. 237-243, Mar. 30, 2007.

R. Dia et al., "Flavouring and Odorant Thiols from Renewable Natural Resources by $In^{III}$-Catalysed Hydrothioacetylation and Lipase-Catalysed Solvolysis", Tetrahedron Letters, vol. 51, No. 16, pp. 2164-2167, Apr. 21, 2010.

T. Zheng et al., "A General and Mild Synthesis of Thioesters and Thiols from Halides", Tetrahedron Letters, vol. 40, pp. 603-606, Jan. 22, 1999.

* cited by examiner

*Primary Examiner* — Joseph Kosack
(74) *Attorney, Agent, or Firm* — Wenderoth, Lind & Ponack, L.L.P.

(57) ABSTRACT

The present invention provides a method for producing sulfur-containing carboxylic acid esters that are useful for aromatizing and flavoring purpose and can cater to the needs for diversified aromatized and/or flavored products, and to further provide a fragrance and/or flavor composition comprising the ester producible by the method and an aromatized and/or flavored product comprising the same.

The sulfur-containing carboxylic acid ester is represented by the following formula (3):

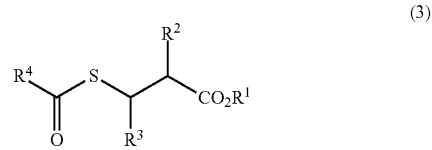

(3)

wherein $R^1$ represents an alkyl group having 1 to 10 carbon atoms or an optionally substituted phenyl group (wherein the substituent thereof is an alkyl group having 1 to 4 carbon atoms or an alkoxy group having 1 to 4 carbon atoms), $R^2$ and $R^3$ independently represent a hydrogen atom, an alkyl group having 1 to 10 carbon atoms or an alkenyl group having 2 to 10 carbon atoms, or $R^2$ and $R^3$ together form an alkylene group, and $R^4$ represents an alkyl group having 1 to 4 carbon atoms.

1 Claim, No Drawings

METHOD FOR PRODUCING SULFUR-CONTAINING CARBOXYLIC ACID ESTERS

TECHNICAL FIELD

The present invention relates to a method for producing sulfur-containing carboxylic acid esters useful as a fragrance and/or flavor ingredient, and to an aromatized and/or flavored product comprising the ester.

BACKGROUND ART

Sulfur-containing compounds have been found in a wide range of foods and botanical essential oils. It is known that sulfur-containing compounds, which generally have extremely low threshold values, are perceived as an unpleasant odor at high concentrations, but give a characteristic aroma, such as a fruity note, at low concentrations and thus are important as an aromatic component.

For example, Patent Literature 1 discloses ethyl 3-mercaptobutyrate as a flavoring agent. Patent Literature 2 discloses ethyl 3-mercaptohexanoate. Further, Patent Literature 3 discloses ethyl 4-thioacetoxybutyrate.

As a method for producing such sulfur-containing compounds, for example, Non Patent Literature 1 describes an overnight reaction of ethyl crotonate with thioacetic acid at 150° C., which gave ethyl 3-acetylthiobutanoate at a yield of 54%. Non Patent Literature 2 describes a reaction of ethyl 2-ethyl-2-propenoate with thioacetic acid (2 Eq), the reaction being performed at 65° C. for 36 hours.

Patent Literature 4 discloses synthesis of ethyl 3-mercapto-2-methylpropionate and ethyl 3-acetylthio-2-methylpropionate by an addition reaction of thioacetic acid to ethyl 2-methyl-2-propenoate. Patent Literature 1 describes production of a compound having a mercapto group by reduction of a disulfide compound obtainable by a reaction of ethyl crotonate with sodium hydrosulfide.

CITATION LIST

Patent Literature

Patent Literature 1: U.S. Pat. No. 6,878,366
Patent Literature 2: U.S. Pat. No. 7,105,194
Patent Literature 3: U.S. Pat. No. 6,899,911
Patent Literature 4: U.S. Pat. No. 5,565,473

Non Patent Literature

Non Patent Literature 1:
Tetrahedron Assym., vol. 5, issue 3, March, 403-410, 1994
Non Patent Literature 2:
J. Med. Chem., 37, 1153-1164, 1994

SUMMARY OF INVENTION

Technical Problem

Such conventional methods require high temperature or prolonged time for the reaction in most cases, resulting in various problems such as substrate degradation and low yield. An object of the present invention is to provide a method for producing sulfur-containing carboxylic acid esters that are useful for aromatizing and flavoring purpose and can cater to the needs for diversified aromatized and/or flavored products, and to further provide a fragrance and/or flavor composition comprising the ester producible by the method and an aromatized and/or flavored product comprising the same.

Solution to Problem

The present inventors conducted intensive research to achieve the above-mentioned object. As a result, they found that an addition reaction of a thiocarboxylic acid to an $\alpha,\beta$-unsaturated carboxylic acid ester in the presence of an acid catalyst gives a sulfur-containing carboxylic acid ester in a single step, and thereby enables quick and high-yield production.

The present invention includes the following.

[1] A method for producing a sulfur-containing carboxylic acid ester represented by the following formula (3):

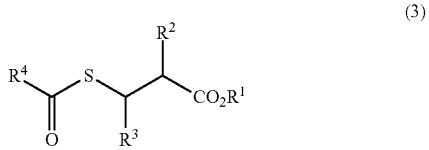

(3)

(wherein $R^1$ represents an alkyl group having 1 to 10 carbon atoms or an optionally substituted phenyl group (wherein the substituent thereof is an alkyl group having 1 to 4 carbon atoms or an alkoxy group having 1 to 4 carbon atoms), $R^2$ and $R^3$ independently represent a hydrogen atom, an alkyl group having 1 to 10 carbon atoms or an alkenyl group having 2 to 10 carbon atoms, or $R^2$ and $R^3$ together form an alkylene group, and $R^4$ represents an alkyl group having 1 to 4 carbon atoms),
the method comprising a reaction of, in the presence of an acid catalyst, an $\alpha,\beta$-unsaturated carboxylic acid ester represented by the following general formula (1):

(1)

(wherein $R^1$, $R^2$ and $R^3$ have the same meanings as defined above, and the wavy line represents cis or trans configuration), with a thiocarboxylic acid represented by the following general formula (2):

(2)

(wherein $R^4$ has the same meaning as defined above).

[2] The method according to the above [1], wherein the acid catalyst to be used is at least one kind selected from para-toluenesulfonic acid and a hydrate thereof; a pyridine salt of para-toluenesulfonic acid; naphthalenesulfonic acid and a hydrate thereof; methanesulfonic acid; camphorsulfonic acid and a hydrate thereof; sulfuric acid; acetic acid; trifluoroacetic acid; chloroacetic acid; and hydrochloric acid.

[3] A method for producing a 3-mercaptocarboxylic acid ester represented by the following general formula (4):

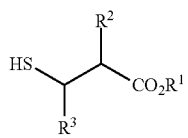

(4)

(wherein $R^1$ represents an alkyl group having 1 to 10 carbon atoms or an optionally substituted phenyl group (wherein the substituent thereof is an alkyl group having 1 to 4 carbon atoms or an alkoxy group having 1 to 4 carbon atoms), and $R^2$ and $R^3$ independently represent a hydrogen atom, an alkyl group having 1 to 10 carbon atoms or an alkenyl group having 2 to 10 carbon atoms, or $R^2$ and $R^3$ together form an alkylene group),
the method comprising deacylation of the sulfur-containing carboxylic acid ester producible by the method according to the above [1] or [2], the sulfur-containing carboxylic acid ester being represented by the general formula (3):

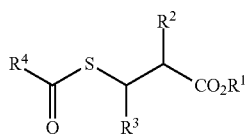

(3)

(wherein $R^1$ represents an alkyl group having 1 to 10 carbon atoms or an optionally substituted phenyl group (wherein the substituent thereof is an alkyl group having 1 to 4 carbon atoms or an alkoxy group having 1 to 4 carbon atoms), $R^2$ and $R^3$ independently represent a hydrogen atom, an alkyl group having 1 to 10 carbon atoms or an alkenyl group having 2 to 10 carbon atoms, or $R^2$ and $R^3$ together form an alkylene group, and $R^4$ represents an alkyl group having 1 to 4 carbon atoms),
in an alcohol having 1 to 10 carbon atoms, in the presence of an alkali metal alkoxide having 1 to 10 carbon atoms or an alkali metal carbonate.
[4] A fragrance and/or flavor composition comprising at least one of the carboxylic acid esters producible by the method according to any one of the above [1] to [3], the carboxylic acid esters being represented by the general formulae (3) and (4).
[5] A food and beverage, cosmetic, detergent, softener, air freshener, deodorant, bath salt or pharmaceutical product comprising the fragrance and/or flavor composition according to the above [4].

Advantageous Effects of Invention

According to the present invention, sulfur-containing carboxylic acid esters with an excellent aroma can be obtained in good yield and purity.

DESCRIPTION OF EMBODIMENTS

Hereinafter, the present invention will be described in detail.
Regarding the method of the present invention, the groups represented by $R^1$, $R^2$ and $R^3$ in the compounds of the general formulae (1), (3) and (4) will be described. $R^1$ represents an alkyl group having 1 to 10 carbon atoms or an optionally substituted phenyl group (wherein the substituent thereof is an alkyl group having 1 to 4 carbon atoms or an alkoxy group having 1 to 4 carbon atoms), and $R^2$ and $R^3$ independently represent a hydrogen atom, an alkyl group having 1 to 10 carbon atoms or an alkenyl group having 2 to 10 carbon atoms, or $R^2$ and $R^3$ together form an alkylene group.

Examples of the alkyl group having 1 to 10 carbon atoms represented by $R^1$, $R^2$ and $R^3$ include a straight or branched, or cyclic alkyl group. Examples of the straight or branched alkyl group include methyl, ethyl, n-propyl, isopropyl, n-butyl, isobutyl, s-butyl, t-butyl, n-pentyl, n-hexyl, n-heptyl, n-octyl, n-nonyl, n-decyl, isopentyl, 1-methylbutyl, 2-methylbutyl, 1-ethylpropyl, isohexyl, 1-methylpentyl, 2-methylpentyl, 3-methylpentyl, 1-ethylbutyl, 2-ethylbutyl and 2-ethylhexyl groups. Examples of the cyclic alkyl group (i.e., cycloalkyl group) include cyclopentyl, cyclohexyl, cycloheptyl and cyclooctyl groups. Examples of the alkenyl group having 2 to 10 carbon atoms represented by $R^2$ and $R^3$ include a straight or branched, or cyclic alkenyl group. Specific examples of the alkenyl group include ethenyl, propenyl, butenyl, pentenyl, hexenyl, heptenyl, octenyl, nonenyl and decenyl groups. The alkenyl group may have a double bond in any position.

The substituent of the optionally substituted phenyl group represented by $R^1$ is an alkyl or alkoxy group having 1 to 4 carbon atoms. Specific examples of the alkyl group include methyl, ethyl, n-propyl, isopropyl, n-butyl, isobutyl, s-butyl and t-butyl groups. Specific examples of the alkoxy group include methoxy, ethoxy, n-propoxy, isopropoxy, n-butoxy, isobutoxy, s-butoxy and t-butoxy groups.

Examples of the alkylene group which may be formed of $R^2$ and $R^3$ include an alkylene group having 3 to 14 carbon atoms, and specific examples thereof include trimethylene, tetramethylene, pentamethylene, hexamethylene, octamethylene, decamethylene, dodecamethylene, tridecamethylene and hexadecamethylene groups. These alkylene groups may be substituted at one or more positions with an alkyl group having 1 to 4 carbon atoms.

In the method of the present invention, examples of the thiocarboxylic acid represented by the general formula (2) include a thiocarboxylic acid having 2 to 5 carbon atoms, and examples of the alkyl group having 1 to 4 carbon atoms represented by $R^4$ in the general formula (2) include a straight or branched, or cyclic alkyl group. Examples of the straight or branched alkyl group include methyl, ethyl, n-propyl, isopropyl, n-butyl, isobutyl, s-butyl and t-butyl groups. As the thiocarboxylic acid, thioacetic acid is preferred. The amount of the thiocarboxylic acid to be used is preferably 0.5- to 20-fold molar excess, and more preferably 1- to 5-fold molar excess relative to the α,β-unsaturated carboxylic acid ester, which is a starting material. Even though a larger amount of the thiocarboxylic acid shortens the reaction time, in consideration of post-treatment of the reaction, the appropriate amount is used depending on the substrate for the reaction.

Examples of the acid catalyst to be used in the present invention include inorganic acids, such as sulfuric acid and hydrochloric acid; organic acids, such as acetic acid, trifluoroacetic acid and chloroacetic acid; and sulfonic acids, such as para-toluenesulfonic acid, naphthalenesulfonic acid, methanesulfonic acid, benzenesulfonic acid and camphorsulfonic acid. Inter alia, sulfonic acids are preferred, and para-toluenesulfonic acid or a pyridine salt of para-toluenesulfonic acid is particularly preferred. The above-mentioned acids can exist as a hydrate, and hydrates thereof are also usable as the acid catalyst.

The reaction in the present invention can be performed in a solvent-free environment or in a solvent. The solvent to be used is not particularly limited as long as it does not give any adverse effects on the production method of the present invention. Examples of the solvent include benzene, toluene, xylene, mesitylene, hexane, heptane, (substituted) cyclohexane, methyl acetate, ethyl acetate, butyl acetate, diethyl ether, diisopropyl ether, tetrahydrofuran, methyl tert-butyl ether and cyclopentyl methyl ether. These solvents may be used alone or as a mixture of two or more kinds thereof. The amount of the solvent to be used is not particularly limited, but is preferably 0.1 to 20 parts by mass, and more preferably 0.5 to 5 parts by mass relative to 1 part by mass of the α,β-unsaturated carboxylic acid ester, which is a starting material. The reaction temperature in the present invention is not particularly limited as long as it does not give any adverse effects on the production method of the present invention, but the temperature is preferably 20 to 200° C., and more preferably 40 to 120° C. The reaction time can be 0.5 to 60 hours, but is preferably 3 to 30 hours, and from an economic standpoint, preferably 1 to 30 hours.

Next, the deacylation step comprised in the production method of the present invention will be described. The 3-mercaptocarboxylic acid ester represented by the above general formula (4) can be produced by deacylation of the sulfur-containing carboxylic acid ester obtainable as described above, which is represented by the general formula (3), in an alcohol having 1 to 10 carbon atoms, in the presence of an alkali metal alkoxide having 1 to 10 carbon atoms or an alkali metal carbonate.

In the deacylation step of the present invention, the alcohol to be used as the solvent and the metal alkoxide to be used as the deacylating aid are each, for example, the one having the alkyl group having 1 to 10 carbon atoms exemplified above in the description of $R^1$. In consideration of the possibility of transesterification, it is preferred to use the alcohol and the metal alkoxide each having the same backbone as that of the alcohol residue of the 3-acylthiocarboxylic acid ester to be deacylated. Specific examples of the alcohol include ethanol. Specific examples of the metal alkoxide include sodium ethoxide. The alkali metal carbonate is not particularly limited, and examples thereof include sodium bicarbonate, sodium carbonate, potassium bicarbonate, potassium carbonate, magnesium carbonate and calcium carbonate. The amount of the alcohol to be used can be appropriately determined, and is not particularly limited. The amount of the metal alkoxide to be used is not particularly limited, but is preferably 0.1 to 5 Eq, and more preferably 0.5 to 2 Eq relative to the sulfur-containing carboxylic acid ester.

The temperature for deacylation is not particularly limited, but is usually −70 to 100° C., and preferably −30 to 50° C. The reaction time is preferably 0.5 to 20 hours, and more preferably 0.5 to 5 hours. The technique to be used for purification (isolation) of the objective compound from the post-reaction mixture is not particularly limited, and conventional techniques, for example, extraction, distillation, recrystallization, etc. can be used.

EXAMPLES

Hereinafter, the present invention will be illustrated in detail by examples shown below, but is not limited thereto. The analysis of purity etc. was performed by gas chromatography (GC). The column used for the analysis is as follows.
Capillary column: TC-1 (15 m×0.53 mm)
Column temperature: 50→250° C. (rising rate: 10° C./min)
Injection temperature: 250° C.
Detector temperature: 250° C.

Example 1

Synthesis of ethyl 3-acetylthio-2-methylbutyrate

A mixture of 51.27 g (0.40 mol) of ethyl tiglate, 76.12 g (1.00 mol) of thioacetic acid, and 7.60 g (0.04 mol) of para-toluenesulfonic acid was stirred under nitrogen atmosphere at 75° C. for 24 hours. After cooling, diethyl ether and a saturated aqueous sodium bicarbonate solution were added to the reaction mixture. The organic layer was separated and washed twice with brine. The solvent in the organic layer was evaporated off, and vacuum distillation (68 to 71° C./2 torr) was performed to give 76.36 g of the objective compound (GC purity: 98.3%, yield: 91.8%, diastereomer ratio: 80.9/19.1).

Examples 2 to 8

The same procedure as described in Example 1 was performed on various α,β-unsaturated carboxylic acid esters. The results are shown in the following Table 1, and the obtained sulfur-containing carboxylic acid esters are collectively represented by the following formula (3'). The purity in the table means GC purity.

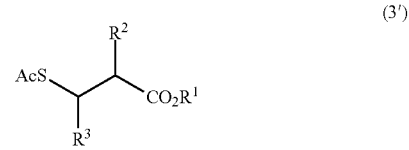

(3')

(In the formula, Ac represents an acetyl group, and $R^1$, $R^2$ and $R^3$ each represent the groups as shown in the following Table 1, or a hydrogen atom.)

TABLE 1

| Example | $R^1$ | $R^2$ | $R^3$ | Time (hr) | Yield (%) | Purity (%) |
|---------|-------|-------|-------|-----------|-----------|------------|
| 2 | Et | H | Me | 5 | 87.5 | 99.3 |
| 3 | i-Bu | H | Me | 4 | 91.5 | 99.5 |
| 4 | Me | Me | Me | 24 | 80.4 | 99.5 |
| 5 | i-Bu | Me | Me | 24 | 85.9 | 98.1 |
| 6 | Et | H | n-Pr | 6 | 84.7 | 99.6 |
| 7 | Et | H | n-$C_7H_{15}$ | 5 | 86.9 | 99.1 |
| 8 | Et | H | Ph | 30 | 87.1 | 98.1 |

(In the table, Me represents a methyl group, Et represents an ethyl group, i-Bu represents an isobutyl group, n-Pr represents a n-propyl group, and Ph represents a phenyl group.)

Example 9

Synthesis of ethyl 3-mercapto-2-methylbutyrate

Under nitrogen atmosphere, a mixture of 40.00 g (0.192 mol) of ethyl 3-acetylthio-2-methylbutyrate and 800 ml of ethanol was cooled to −15° C., 72.01 g (0.212 mol, 1.1 Eq) of a 20% solution of sodium ethoxide in ethanol was added dropwise thereto over 1 hour, and the mixture was stirred for 3 hours. The reaction mixture was neutralized with 15.00 g of acetic acid, and then ethanol was evaporated off under reduced pressure. After addition of an aqueous sodium chloride solution to the residue, extraction with diethyl ether was performed. The organic layer was washed successively with a saturated aqueous sodium bicarbonate solution and brine (twice). The solvent in the organic layer was evaporated off, and vacuum distillation (35 to 36° C./2 torr) was performed to give 17.63 g of the objective compound (GC purity: 99.3%, yield: 56.1%, diastereomer ratio: 80.6/19.4).

Examples 10 to 16

The same procedure as described in Example 9 was performed on various 3-acetylthiocarboxylic acid esters. The results are shown in the following Table 2, and the obtained 3-mercaptocarboxylic acid esters are collectively represented by the following formula (4). The purity in the table means GC purity.

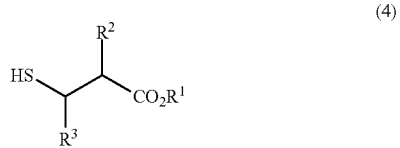

(4)

(In the formula, $R^1$, $R^2$ and $R^3$ each represent the groups as shown in the following Table 2, or a hydrogen atom.)

TABLE 2

| Example | $R^1$ | $R^2$ | $R^3$ | Yield (%) | Purity (%) |
|---|---|---|---|---|---|
| 10 | Et | H | Me | 41.7 | 99.8 |
| 11 | i-Bu | H | Me | 45.9 | 99.6 |
| 12 | Me | Me | Me | 56.2 | 99.8 |
| 13 | i-Bu | Me | Me | 67.3 | 99.5 |
| 14 | Et | H | n-Pr | 65.2 | 99.5 |
| 15 | Et | H | n-$C_7H_{15}$ | 60.2 | 98.3 |
| 16 | Et | H | Ph | 60.2 | 95.7 |

(In the table, Me represents a methyl group, Et represents an ethyl group, i-Bu represents an isobutyl group, n-Pr represents a n-propyl group, and Ph represents a phenyl group.)

Comparative Example

Synthesis of ethyl 3-acetylthio-2-methylbutyrate (in the Absence of the Acid Catalyst)

A mixture of 3.20 g (0.025 mol) of ethyl tiglate and 4.76 g (0.0625 mol) of thioacetic acid was prepared and allowed to react under nitrogen atmosphere at 85° C. for 24 hours. The results showed that the conversion rate of ethyl tiglate was 35.3%, and that the selectivity for the objective compound was 91.6%.

Example 17

Preparation of Fragrance and/or Flavor Composition

Ethyl 3-mercapto-2-methylbutyrate synthesized in Example 9 was diluted to 0.01% with triethyl citrate (TEC), and thus, a fragrance and/or flavor composition was prepared.

Example 18

Preparation of Floral Fragrance and/or Flavor 100 g of the floral fragrance and/or flavor as shown in the following Table 3, which contains 3% by weight of the fragrance and/or flavor composition prepared in Example 17, was prepared.

TABLE 3

| Ingredient | wt % |
|---|---|
| Acetyl isoeugenol | 0.15 |
| TEC solution of ethyl 3-mercapto-2-methylbutyrate (0.01%) | 3.0 |
| Allyl caproate | 5.0 |
| Anisyl propionate | 0.05 |
| Benzyl isovalerate | 1.0 |
| Benzaldehyde | 0.02 |
| Butyl benzoate | 0.2 |
| L-Citronellyl propionate | 0.1 |
| δ-Decalactone | 0.25 |
| 1,1-Dimethyl-2-phenethyl butyrate | 23.5 |
| Dipropylene glycol | 53.73 |
| Ethyl acetate | 0.2 |
| Ethyl amyl ketone | 0.1 |
| Ethyl butyrate | 2.0 |
| Ethyl decanoate | 0.1 |
| Ethyl caproate | 0.01 |
| Ethyl caprylate | 0.1 |
| Ethyl isovalerate | 0.1 |
| Ethyl propionate | 0.1 |
| Trans-2-hexenol | 2.5 |
| Isoamyl isobutyrate | 0.1 |
| Isobornyl acetate | 0.5 |
| Lemon oil | 0.2 |
| Methyl isovalerate | 0.1 |
| Phenethyl isovalerate | 6.0 |
| δ-Undecalactone | 0.2 |
| γ-Undecalactone | 0.2 |
| Vanillin | 0.3 |
| Total | 100.0 |

INDUSTRIAL APPLICABILITY

According to the present invention, sulfur-containing carboxylic acid esters useful for aromatizing and flavoring purpose can be obtained in good yield and purity. Further, a fragrance and/or flavor composition comprising the ester, and an aromatized and/or flavored product comprising the same can be provided.

The invention claimed is:
1. A method for producing a sulfur-containing carboxylic acid ester represented by the following formula (3):

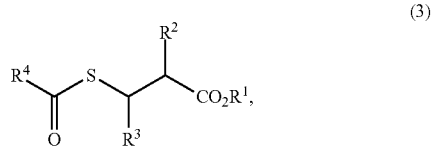

(3)

wherein
$R^1$ represents an alkyl group having 1 to 10 carbon atoms or an optionally substituted phenyl group, wherein the substituent thereof is an alkyl group having 1 to 4 carbon atoms or an alkoxy group having 1 to 4 carbon atoms,
$R^2$ and $R^3$ independently represent a hydrogen atom, an alkyl group having 1 to 10 carbon atoms or an alkenyl group having 2 to 10 carbon atoms, or $R^2$ and $R^3$ together form an alkylene group, and
$R^4$ represents an alkyl group having 1 to 4 carbon atoms, the method comprising a reaction of, in the presence of an acid catalyst, an α,β-unsaturated carboxylic acid ester represented by the following general formula (1):

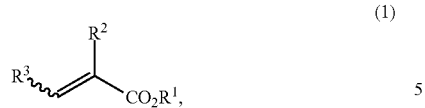 (1)

wherein $R^1$, $R^2$ and $R^3$ have the same meanings as defined above, and the wavy line represents cis or trans configuration,
with a thiocarboxylic acid represented by the following general formula (2):

 (2)

wherein $R^4$ has the same meaning as defined above),
wherein the acid catalyst is at least one kind selected from the group consisting of a para-toluenesulfonic acid or a hydrate thereof; a pyridine salt of para-toluenesulfonic acid; naphthalenesulfonic acid or a hydrate thereof; methanesulfonic acid; camphorsulfonic acid or a hydrate thereof; sulfuric acid; acetic acid; trifluoroacetic acid; chloroacetic acid; and hydrochloric acid.

* * * * *